(12) United States Patent
Hua et al.

(10) Patent No.: US 12,313,510 B2
(45) Date of Patent: May 27, 2025

(54) KIT FOR EXTRACTING MYCOTOXIN RESIDUES IN AGRICULTURAL PRODUCTS AND METHOD OF OBTAINING PRIMARY TEST LIQUID FROM AGRICULTURAL PRODUCTS USING THE SAME

(71) Applicant: GREAT ENGINEERING TECHNOLOGY CORPORATION, Kaohsiung (TW)

(72) Inventors: Hung-Ta Hua, Kaohsiung (TW); Tseng-Yu Tsai, Kaohsiung (TW); Yi-Jia Ku, Kaohsiung (TW)

(73) Assignee: GREAT ENGINEERING TECHNOLOGY CORPORATION, Kaohsiung (TW)

( * ) Notice: Subject to any disclaimer, the term of this patent is extended or adjusted under 35 U.S.C. 154(b) by 217 days.

(21) Appl. No.: 18/206,320

(22) Filed: Jun. 6, 2023

(65) Prior Publication Data

US 2024/0133781 A1  Apr. 25, 2024
US 2024/0230487 A9  Jul. 11, 2024

(30) Foreign Application Priority Data

Oct. 20, 2022  (TW) .................................. 111139853

(51) Int. Cl.
   *G01N 1/40*  (2006.01)

(52) U.S. Cl.
   CPC ... *G01N 1/4005* (2013.01); *G01N 2001/4011* (2013.01)

(58) Field of Classification Search
   CPC .......... G01N 1/4005; G01N 1/28; G01N 1/34; G01N 1/40; G01N 1/405; G01N 2001/4011
   See application file for complete search history.

(56) References Cited

U.S. PATENT DOCUMENTS 5,178,832 A   1/1993  Phillips et al.
9,581,579 B2  2/2017  Lin
(Continued)

FOREIGN PATENT DOCUMENTS

CN   108051279 A   5/2018
CN   209570424 U   11/2019
(Continued)

OTHER PUBLICATIONS

Espacenet English Translation of CN115025518A. (Year: 2022).*

*Primary Examiner* — Kathryn Elizabeth Limbaugh
(74) *Attorney, Agent, or Firm* — WPAT, PC

(57) ABSTRACT

A kit for extracting mycotoxin residues in agricultural products according to the present disclosure includes a pipe, a first powder mixture layer and a second powder mixture layer. The pipe has an output port at the bottom thereof and an input port at the top thereof for inputting a sample solution. The first powder mixture layer is in the form of powder and filled in the pipe. The first powder mixture layer contains cation exchange resin powder, C18 and diatomaceous earth powder. The second powder mixture layer is in the form of powder and filled in the pipe. The second powder mixture layer is located below the first powder mixture layer and above the output port. The second powder mixture layer contains PSA powder, anhydrous magnesium sulfate powder, activated carbon, PLS powder, diatomaceous earth powder and C18 powder. The present disclosure further provides a method of obtaining a primary test liquid from agricultural products using the above kit.

15 Claims, 2 Drawing Sheets

(56) References Cited

U.S. PATENT DOCUMENTS

| | | |
|---|---|---|
| 11,480,505 B2 | 10/2022 | Hua |
| 2007/0117222 A1 | 5/2007 | Sibanda et al. |
| 2009/0035786 A1 | 2/2009 | Zabe et al. |

FOREIGN PATENT DOCUMENTS

| | | | |
|---|---|---|---|
| CN | 114383919 A | 4/2022 | |
| CN | 115025518 A | 9/2022 | |
| WO | WO-2008113365 A2 * | 9/2008 | ............ B01L 3/5082 |

\* cited by examiner

KIT FOR EXTRACTING MYCOTOXIN RESIDUES IN AGRICULTURAL PRODUCTS AND METHOD OF OBTAINING PRIMARY TEST LIQUID FROM AGRICULTURAL PRODUCTS USING THE SAME

CROSS-REFERENCE TO RELATED APPLICATIONS

The present application is based on and claims priority to Taiwanese Application Number 111139853, filed Oct. 20, 2022, the disclosure of which is hereby incorporated by reference herein in its entirety.

FIELD OF THE DISCLOSURE

This disclosure relates to a kit for extracting mycotoxin residues in agricultural products and method of obtaining primary test liquid from agricultural products using the same.

BACKGROUND OF THE DISCLOSURE

Mycotoxins are toxins produced by the growth of molds in agricultural products such as grains. In general, agricultural products include peanuts, corn, soybeans, rice and wheat. The livestock industry also needs to detect the content of mycotoxins in feed.

In order to detect the amount of mycotoxin residues in food, a number of extraction kits have been developed. However, different extraction kits and detecting methods are currently used for the detections of different types of mycotoxins in agricultural products, or multiple mycotoxins can be detected at the same time, but all of them need to use the enzyme immunoaffinity extraction kits that are expensive and require low temperature storage.

For example, in order to detect mycotoxin residues such as Aflatoxin B1, Aflatoxin B, Aflatoxin G1, Aflatoxin G2, Deoxynivalenol, Fumonisin B1, Fumonisin B2, HT-2 toxin, Ochartoxin A, T-2 toxin and Zearalenone in food, the government has issued different extraction kits and detecting methods.

SUMMARY

In order to solve the problem of using different extraction kits and methods of detecting different types of mycotoxin residues in food, the present disclosure provides a kit for extracting mycotoxin residues in agricultural products and method of obtaining primary test liquid from agricultural products using the same.

In one embodiment, the kit for extracting mycotoxin residues in agricultural products according to the present disclosure includes a pipe, a first powder mixture layer and a second powder mixture layer. The pipe has an output port at the bottom thereof and an input port at the top thereof for inputting a sample solution. The first powder mixture layer is in the form of powder and filled in the pipe. The first powder mixture layer contains cation exchange resin powder, C18 and diatomaceous earth powder. The second powder mixture layer is in the form of powder and filled in the pipe. The second powder mixture layer is located below the first powder mixture layer and above the output port. The second powder mixture layer contains PSA powder, anhydrous magnesium sulfate powder, activated carbon, PLS powder, diatomaceous earth powder and C18 powder.

In another embodiment, the method of obtaining a primary test liquid from an agricultural sample includes the steps: homogenizing the sample; shaking the homogenized sample with an extraction solvent to obtain a sample solution; adding the sample solution into the pipe of the above kit; and driving the sample solution in the pipe to flow through the first powder mixture layer and the second powder mixture layer in the pipe in sequence to output from the output port of the pipe a primary test liquid.

When the kit of the present disclosure is used to obtain primary test liquid from 20 samples, the consumption of the extraction solvent may be saved by 35-90%, and the operation time for extraction may be saved by 80-95%.

Furthermore, according to the kit of the present disclosure and the method of obtaining the primary test liquid, 11 types of mycotoxin residues in food for animal use, including Aflatoxin B1, Aflatoxin B, Aflatoxin G1, Aflatoxin G2, Deoxynivalenol, Fumonisin B1, Fumonisin B2, HT-2 toxin, Ochartoxin A, T-2 toxin and Zearalenone may be simultaneously detected. In comparison with the current method issued by government, detection of different types of mycotoxin residues needs different detection methods.

BRIEF DESCRIPTION OF DRAWINGS

Other objects, advantages, and novel features of the present disclosure will become more apparent from the following detailed description when taken in conjunction with the accompanying drawings.

DETAILED DESCRIPTION OF THE DISCLOSURE

It should be noted that, wherever possible, the same reference numbers will be used throughout the drawings to refer to the same or like parts.

Figure 1:
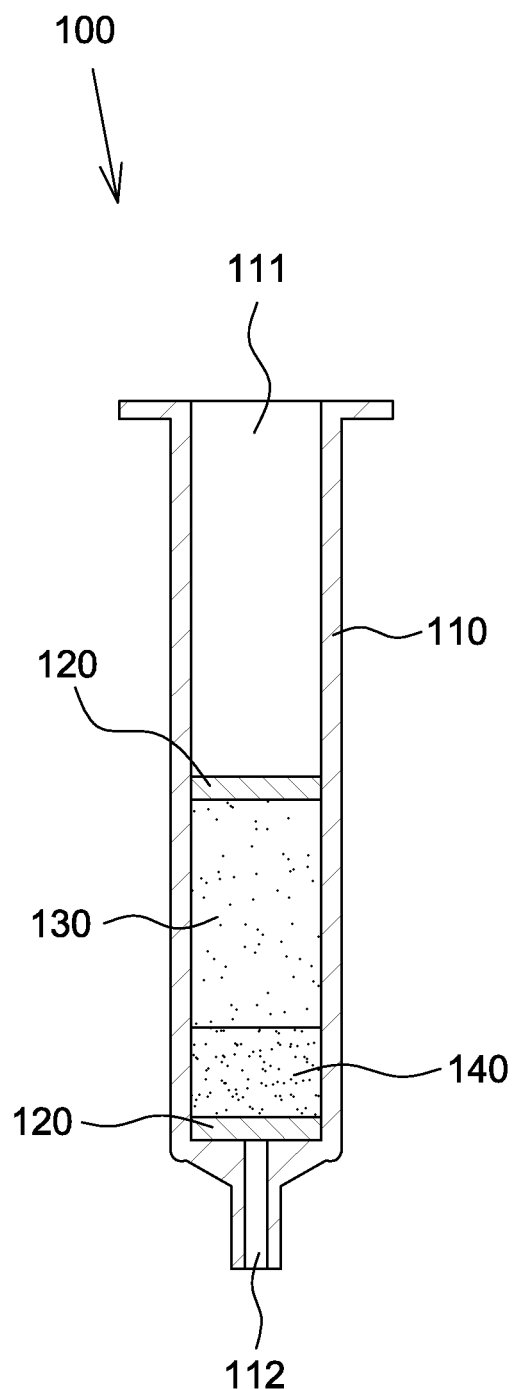
FIG. 1 is a schematic diagram of an extraction kit according to a preferred embodiment of the present disclosure.

Referring to FIG. 1, there is shown an extraction kit 100 of the present disclosure for extracting mycotoxin residues from agricultural products. The extraction kit 100 for extracting mycotoxin residues from agricultural products of the present disclosure includes a pipe 110, a first powder mixture layer 130 filled in the pipe 110 and a second powder mixture layer 140 filled in the pipe 110. The pipe 110 is preferably a cylindrical pipe having an output port 112 at the bottom thereof and an input port 111 at the top thereof. The first powder mixture layer 130 is located below the input port 111, and the second powder mixture layer 140 is located below the first powder mixture layer 130 and above the output port 112. Besides, the extraction kit 100 of the present disclosure further includes two filter pads 120, wherein one of the filter pads 120 is fixed on the top surface of the first powder mixture layer 130 and the other filter pad 120 is fixed on the bottom surface of the second powder mixture layer 140. The top surface of the second powder mixture layer 140 is in direct contact with the first powder mixture layer 130. Alternatively, a filter pad (not shown in the figure) may be further inserted between the first powder mixture layer 130 and the second powder mixture layer 140 to prevent them from mixing.

The extraction kit 100 mentioned above is used in a procedure of detecting mycotoxin residues in agricultural products. This procedure includes the method of obtaining a primary test liquid from an agricultural sample using the extraction kit 100 of the present disclosure. The method includes the following steps.

The agricultural sample is first homogenized by using a homogenizer so that the sample is processed into fragments of the agricultural sample. The agricultural samples are taken from peanuts, corn, soybeans, rice or wheat, for use as detected samples of mycotoxin residue detection.

Figure 2:
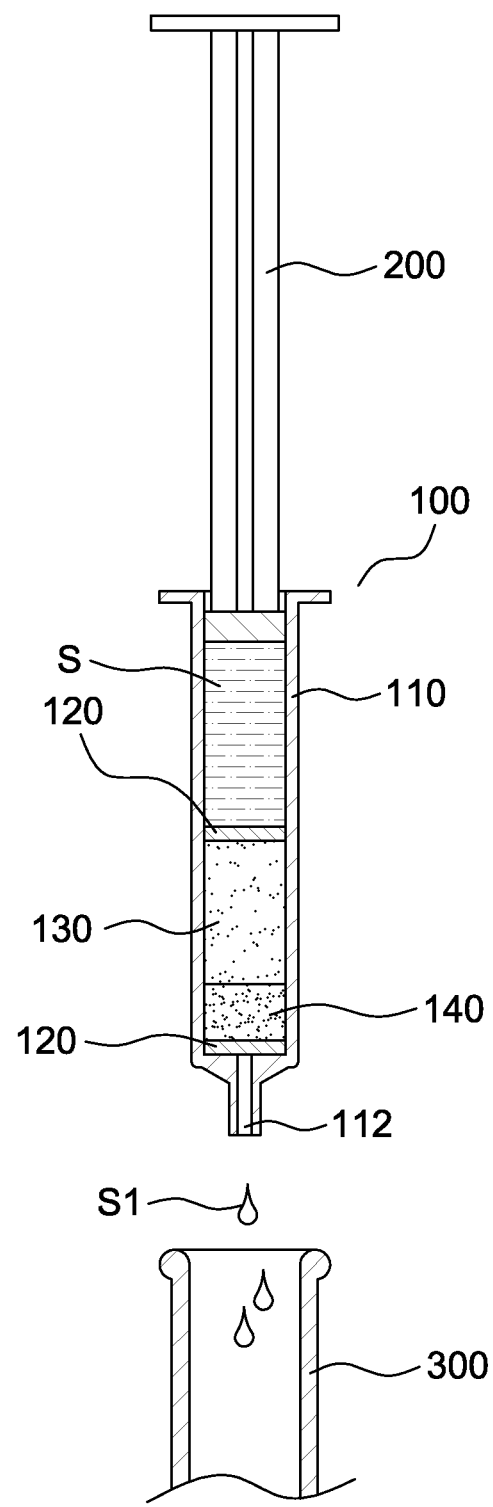
FIG. 2 is another schematic diagram of an extraction kit according to a preferred embodiment of the present disclosure.

Afterward, an extraction solvent is added to the above agricultural sample and shaken strongly to obtain a sample solution S. A (2~4)±0.03 grams of the agricultural sample needs to be added to 1 to 20 mL of extraction solvent. The extraction solvent is formic acid-containing acetonitrile water (with 50-80% acetonitrile). A (2~4)±0.03 grams of the agricultural sample is preferably added with 5 mL of the aforementioned extraction solvent. The extraction solvent is preferably 0.5% formic acid-containing acetonitrile water (with 50-80% acetonitrile). The sample solution S is then added into the pipe 110 of the extraction kit 100, as shown in FIG. 2.

Finally, the sample solution S in the pipe 110 is driven to flow through the first powder mixture layer 130 and the second powder mixture layer 140 in sequence so as to output a primary test liquid from the output port 112 of the pipe 110. One of the ways of driving the sample solution S to flow through the first powder mixture layer 130 and the second powder mixture layer 140 in sequence is to press a piston rod 200 to drive the sample solution S to flow. In addition, an air exhausting method may also be used to drive the sample solution S in the pipe 110 to flow through the first powder mixture layer 130 and the second powder mixture layer 140 in sequence. In the air exhausting method a suction device including a vacuum pump (not shown in the figures) is used to connect the output port 112. The vacuum pump is then powered to suck the sample solution S in the pipe 110 to flow out of the output port 112. A flow rate of the sample solution S is preferably controlled to a range of 0.01 to 0.2 mL/sec, more preferably to 0.05 mL/sec. It is to be noted that the filter pads 120 mentioned above should be one without affecting the aforementioned flow rate.

The powder mixture in the first powder mixture layer 130 is able to adsorb most of the interfering impurities in the sample solution S. Therefore, most of the interfering impurities in the sample solution S are kept in the first powder mixture layer 130 after the sample solution S flows through the first powder mixture layer 130. Furthermore, the powder mixture in the second powder mixture layer 140 is able to adsorb the water in the sample solution S and the impurities, such as oil or pigment, which may interfere with the instruments when the sample solution S flows through the second powder mixture layer 140. Therefore, after the sample solution S flows through the second powder mixture layer 140, it will turn into a primary test liquid S1 without impurities or with few impurities. The primary test liquid S1 may be collected with a tube 300.

The primary test liquid S1 may be directly detected by a liquid chromatograph tandem mass spectrometer (LC/MS/MS) to ensure that the mycotoxin residues in the sample comply with a requirement. Alternatively, the primary test liquid S1 may also be subjected to a step of air-drying, a step of adding methanol water and a step of filtering with a filter in sequence and then be detected by a liquid chromatography tandem mass spectrometer (LC/MS/MS).

The total weight of the first powder mixture layer 130 is 0.1 to 1 gram, preferably 0.155 gram. The pipe 110 has a selected inner diameter so that the first powder mixture layer 130 has not been pressed tightly and is loose or fluffy during a process of being filled in the pipe 110 with the selected inner diameter. From the viewpoint of volume, the first powder mixture layer 130 has an area of 0.5 to 0.6 cm$^2$ in the pipe 110, preferably 0.5 cm$^2$, and a height of 0.1 to 0.8 cm, preferably 0.2 cm. Therefore, the total volume of the first powder mixture layer 130 is preferably 0.1 cm$^3$ and the density of the first powder mixture layer 130 is preferably 1.55 g/cm$^3$. Further, the first powder mixture layer 130 has a porosity of 35 to 70% in the pipe 110, preferably 50% to 62%, so that the flow rate of the sample solution S flowing through the first powder mixture layer 130 may be controlled in an expected range. This makes most of the interfering impurities in the sample solution S removed by the first powder mixture layer 130.

The above porosity is defined as (the total volume of the first powder mixture layer 130 filled in the pipe 110−the real volume of the first powder mixture layer 130)/(the total volume of the first powder mixture layer 130 filled in the pipe 110)×100%.

In the present disclosure, the powder components used in the first powder mixture layer 130 includes cation exchange resin powder, C18 (Octadecylsilane) and diatomaceous earth powder, which are uniformly mixed in the first powder mixture layer 130. Further, the first powder mixture layer 130 is preferably a mixture of cation exchange resin powder, C18 and diatomaceous earth powder, and the weight ratio of the cation exchange resin powder, C18 and diatomaceous earth powder in the first powder mixture layer 130 is 1:(1~4):0.1, preferably 1:2:0.1.

In the present disclosure, the second powder mixture layer 140 has a weight of 0.2 to 2.0 grams, preferably 0.67 gram. From the viewpoint of volume, the second powder mixture layer 140 has an area of 0.5 to 0.6 cm$^2$ in the pipe 110, preferably 0.5 cm$^2$, and a height of 0.5 to 2.5 cm, preferably 0.6 cm.

In the present disclosure, the powder component used in the second powder mixture layer 140 includes PSA (primary secondary amine) powder, anhydrous magnesium sulfate powder, activated carbon, PLS (polystyrene-divinylbenzene (PS-DVB) copolymer) powder, diatomaceous earth powder and C18 powder, which are uniformly mixed in the second powder mixture layer 140. Further, the second powder mixture layer 140 is preferably a mixture of PSA powder, anhydrous magnesium sulfate powder, activated carbon, PLS powder, diatomaceous earth powder and C18 powder, and the weight ratio of the PSA powder, anhydrous magnesium sulfate powder, activated carbon, PLS powder, diatomaceous earth powder and C18 powder in the second powder mixture layer 140 is 2.5:60:1:1:1.5:(1~4), preferably 2.5:60:1:1:1.5:1.

It is apparent from the above description that the sample solution S composed of the sample fragments and the extraction solvent may be directly extracted by using the extraction kit 100 of the present disclosure to obtain a primary test liquid. With the use of the extraction kit 100 of the present disclosure, the time taken to obtain a primary test liquid from an agricultural sample may be greatly reduced. Therefore, the detection of mycotoxin residues in the sample may be performed quickly.

For example, when the extraction kit of the present disclosure is used to obtain primary test liquid from 20 samples, the consumption of the extraction solvent may be saved by 35-90%, and the operation time for extraction may be saved by 80-95%.

Furthermore, according to the kit of the present disclosure and the method of obtaining the primary test liquid, 11 types of mycotoxin residues in food for animal use, including Aflatoxin B1, Aflatoxin B, Aflatoxin G1, Aflatoxin G2, Deoxynivalenol, Fumonisin B1, Fumonisin B2, HT-2 toxin, Ochartoxin A, T-2 toxin and Zearalenone may be simultaneously detected. In comparison with the current method issued by government, detection of different types of mycotoxin residues needs different detection methods.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

The invention claimed is:

1. A kit for extracting mycotoxin residues from agricultural products, comprising:

a pipe having an output port at a bottom thereof and an input port at a top thereof, the input port is configured to input a sample solution;

a first powder mixture layer filled in the pipe, the first powder mixture layer including a mixture of cation exchange resin powder, C18 and diatomaceous earth powder; and a second powder mixture layer filled in the pipe and positioned between the first powder mixture layer and the output port, the second powder mixture layer including a mixture of primary secondary amine (PSA) powder, anhydrous magnesium sulfate powder, activated carbon, polystyrene-divinylbenzene copolymer (PLS) powder, diatomaceous earth powder and C18 powder.

2. The kit as claimed in claim 1, wherein a weight ratio of the cation exchange resin powder, the C18 and the diatomaceous earth powder in the first powder mixture layer is 1:(1~4):0.1.

3. The kit as claimed in claim 1, wherein a weight ratio of the PSA powder, the anhydrous magnesium sulfate powder, the activated carbon, the PLS powder, the diatomaceous earth powder and the C18 powder in the second powder mixture layer is 2.5:60:1:1:1.5:(1~4).

4. The kit as claimed in claim 2, wherein the weight ratio of the cation exchange resin powder, the C18 and the diatomaceous earth powder in the first powder mixture layer is 1:2:0.1.

5. The kit as claimed in claim 3, wherein the weight ratio of the PSA powder, the anhydrous magnesium sulfate powder, the activated carbon, the PLS powder, the diatomaceous earth powder and the C18 powder in the second powder mixture layer is 2.5:60:1:1:1.5:1.

6. The kit as claimed in claim 1, wherein the first powder mixture layer has a porosity of 35 to 70% in the pipe.

7. The kit as claimed in claim 1, wherein the first powder mixture layer has an area of 0.5 to 0.6 $cm^2$ and a height of 0.1 to 0.8 cm in the pipe.

8. The kit as claimed in claim 1, wherein the second powder mixture layer has an area of 0.5 to 0.6 $cm^2$ and a height of 0.5 to 2.5 cm in the pipe.

9. A method of obtaining a primary test liquid from an agricultural sample, comprising:

homogenizing a sample;

shaking the homogenized sample with an extraction solvent to obtain a sample solution;

adding the sample solution into the pipe of the kit of claim 1; and driving the sample solution in the pipe to flow through the first powder mixture layer and the second powder mixture layer in the pipe in sequence to output from the output port of the pipe a primary test liquid.

10. The method as claimed in claim 9, wherein a (2~4)±0.03 grams of the sample is added to 1 to 20 mL of the extraction solvent.

11. The method as claimed in claim 9, wherein a (2~4)±0.03 grams of the sample is added to 5 mL of the extraction solvent.

12. The method as claimed in claim 9, wherein the extraction solvent is formic acid-containing acetonitrile water with 50-80% acetonitrile.

13. The method as claimed in claim 12, wherein the extraction solvent is 0.5% formic acid-containing acetonitrile water with 50-80% acetonitrile.

14. The method as claimed in claim 9, wherein a flow rate of the sample solution is controlled in a range of about 0.01 to 0.2 mL/sec.

15. The method as claimed in claim 14, wherein the flow rate of the sample solution is controlled to 0.05 mL/sec.

* * * * *